(12) United States Patent
Galvao

(10) Patent No.: US 6,426,096 B1
(45) Date of Patent: Jul. 30, 2002

(54) ANOREXIGENIC COMPOSITION

(76) Inventor: Paolina Galvao, 3 Flamink Avenue, Douglasdale, Sandton, Gauteng (ZA)

(*) Notice: Subject to any disclaimer, the term of this patent is extended or adjusted under 35 U.S.C. 154(b) by 0 days.

(21) Appl. No.: 09/571,169

(22) Filed: May 16, 2000

Related U.S. Application Data

(63) Continuation-in-part of application No. 09/192,590, filed on Nov. 17, 1998, now abandoned.

(30) Foreign Application Priority Data

Dec. 10, 1997 (ZA) .............................................. 97/11083

(51) Int. Cl.⁷ ....................... A61K 35/78; A61K 31/555; A61K 31/135
(52) U.S. Cl. ........................ 424/725; 514/188; 514/556; 514/649
(58) Field of Search .......................... 424/725; 514/188, 514/556, 649

(56) References Cited

U.S. PATENT DOCUMENTS 5,804,596 A * 9/1998 Majeed et al. ............... 514/455
5,925,377 A * 7/1999 Gerth et al. .................. 424/451
6,262,049 B1 * 7/2001 Coffin et al. ............ 514/213.01

* cited by examiner

*Primary Examiner*—Raymond Henley, III
(74) *Attorney, Agent, or Firm*—Kenyon & Kenyon

(57) ABSTRACT

A method of treating carbohydrate craving in a human patient comprises administering to the patient an anorexigenic composition comprising a compound which elevates serotonin levels in the brain of the patient, typically hypercin, found in St John's Wort Extract, or sibutramine, in a mixture with a physiologically acceptable metabolisable chromium compound. The chromium compound is selected from chromium picolinate, chromium polynicotinate, chromium chelate, chromium proteinate, or any other bioavailable chromium compound. The mixture optionally includes laevorotary carnitine or a racemic mixture of carnitine.

18 Claims, No Drawings

ANOREXIGENIC COMPOSITION

This is a continuation-in-part of U.S. application Ser. No. 09/192,590 filed Nov. 17, 1998, now abandoned.

BACKGROUND OF THE INVENTION

This invention relates to anorexigenic compositions, their use in carbohydrate craving control with consequent weight control of the human body, and to methods of treating carbohydrate craving in a human.

It is reasonably well accepted that obesity is associated with carbohydrate craving at least in the majority of obese persons. Obesity is also associated with metabolic disturbances related to insulin resistance, particularly hyperinsulinaemia and elevated triglyceride levels. Insulin resistance, in turn, is believed to be associated with depressed serotonin levels in the brain which are believed to cause carbohydrate craving to the end that more carbohydrate would cause the insulin levels to rise and counteract the insulin resistance. A vicious circle ensues and obesity in some degree generally follows.

Hypericin which is an extract from the herb St John's Wort, is presently available in the market as a remedy for depression, anxiety and hyperactivity. It is believed to act by inhibiting the enzyme monoamine oxidase (MAO), which is responsible for the breakdown of serotonin in the brain.

Sibutramine is also a compound that has been used for the treatment of depression. It is believed to act as a serotonin re-uptake inhibitor.

Metabolisable chromium compounds such as chromium picolinate, for example, are known as supplements which can have the effects of reducing body fat; retaining and building lean muscles; and lowering elevated blood sugar and cholesterol levels. They have also been shown to have significant effects on elevated circulating insulin levels and insulin resistance.

It has now surprisingly been found that combinations of these compounds exhibit a desirable synergistic effect when employed together in the treatment of obesity, for example.

SUMMARY OF THE INVENTION

In accordance with one aspect of this invention there is provided a method of treating carbohydrate craving in a human patient comprising administering to the patient an anorexigenic composition comprising a compound which elevates serotonin levels in the brain of the patient in a mixture with a physiologically acceptable metabolisable chromium compound.

The compound which elevates serotonin levels in the brain may be hypericin, preferably in the form of St John's Wort Extract, or sibutramine, or a salt thereof, in particular sibutramine hydrochloride monohydrate.

Further features of the invention provide for the chromium compound to be selected from chromium picolinate, chromium polynicotinate, chromium chelate, chromium proteinate, or any other bioavailable chromium compound; and for the mixture to optionally include laevorotary carnitine or a racemic mixture of carnitine.

Preferably the anorexigenic composition is produced in unit dosage form.

In one form of the invention a dosage unit will comprise:

10 mg–1000 mg St John's Wort Extract;
<1000 μg chromium compound; and
0 mg–500 mg L-carnitine.

The dosage unit may conveniently be a capsule or tablet typically containing from 20–150 mg St John's Wort Extract, 80–600 μg chromium compound, preferably as chromium picolinate; and 80–200 mg L-carnitine either alone or in a racemic mixture with D-carnitine.

The dosage unit containing hypericin from St John's Wort Extract is typically administered to the patient as a single capsule taken once to three times daily.

A preferred capsule or tablet comprises:

| | |
|---|---|
| St. John's Wort Extract | 20 mg–150 mg |
| Chromium Picolinate or other bioavailable chromium salt: | 100 μg–300 μg |
| L-carnitane. | 80 mg–150 mg |

In an alternative form of the invention a dosage unit will comprise:

| | |
|---|---|
| 1 mg–30 mg | sibutramine |
| 100 μg–800 μg | chromium compound; and |
| 0 mg–800 mg | L-carnitine. |

Once again the dosage unit can conveniently be a capsule or tablet typically containing 5–20 mg sibutramine, preferably as sibutramine hydrochloride monohydrate, 100–600 μg chromium compound, preferably as chromium picolinate/polynicotinate or other bioavailable salt, and 100–180 mg L-carnitine either alone or in a racemic mixture with D-carnitine.

The dosage unit form containing sibutramine is typically administered to the patient as a single capsule taken once a day. The dosage may be increased, where necessary, to a single capsule twice daily.

DETAILED DESCRIPTION OF PREFERRED EMBODIMENTS

It is generally accepted that obesity is associated with carbohydrate craving in 100% of obese woman and about 70% of obese men. For years scientists have suspected that there is a link between a condition called insulin resistance and carbohydrate craving.

In order to appreciate the manner in which it is believed that the composition of the invention functions, it is important to understand the concept of "Insulin Resistance".

Under normal circumstances, when a patient eats carbohydrates, the following sequence occurs:

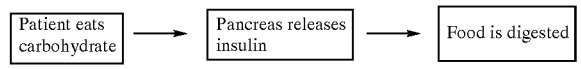

However, in patients who are insulin resistant, the following sequence would appear to take place:

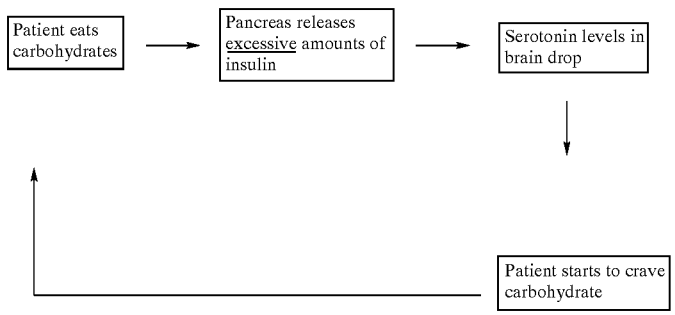

When an excessive amount of insulin is released in insulin resistant patients, their serotonin levels drop. This starts carbohydrate craving which drives them to eat more carbohydrate and a vicious cycle begins. In a relatively short period of time very low serotonin levels are experienced. Symptoms of a low serotonin level include depression, insomnia, lack of libido, fatigue and increased craving for carbohydrate.

The composition of the invention is aimed not only at increasing the levels of serotonin in the brain but also the combating of insulin resistance too. In order to increase the brain's serotonin level the product contains a compound which elevates serotonin levels in the brain, for example hypericin or sibutramine.

It is believed that hypericin works by inhibiting an enzyme called Monoamine Oxidase (MAO). MAO is responsible for the breakdown of serotonin. By inhibiting the breakdown of serotonin it is believed that the brain's serotonin level increases. An increased brain serotonin level will alleviate craving for carbohydrate hence affording the patient greater self-control enabling him to stick to his eating plan.

Sibutramine, on the other hand, works by acting as a serotonin re-uptake inhibitor (as well as by noradrenaline and dopamine re-uptake inhibition). It is believed that sibutramine increases the brain's serotonin levels by inhibiting the re-uptake of serotonin and thus alleviates the craving for carbohydrate.

However, the benefits of simply increasing the brain's serotonin level are limited because in the insulin resistant patient, every time he eats carbohydrate (even as part of a balanced eating plan) excess insulin is released and his serotonin level drops.

In order to counteract this, it is preferable to stop the release of excessive insulin and hence stop the rebound drop in serotonin while at the same time further increasing the serotonin levels using hypericin or sibutramine. It is believed that this can be achieved, at least in part, by including a bioavailable chromium compound in the composition.

Chromium is a component of the dinicotinic acid-gluthathione-chromium complex, the glucose tolerance factor, which enhances insulin sensitivity in a person. However, dietary intake of chromium is generally suboptimal causing chromium deficiency.

Chromium deficiency in turn causes hyperinsulinemia and insulin resistance. Moreover, hyperinsulinemia causes increased urinary chromium loss leading to a vicious cycle.

Chromium supplementation has been shown to have a significant effect on elevated circulating insulin levels, insulin resistance, hypertryglicerimia and decreased HDL cholesterol levels. Chromium supplementation has also been found to decrease LDL cholesterol levels and revert atherosclerotic lesions.

These properties when combined with those of a compound which elevate serotonin levels in the brain provide a two pronged attack on obesity. The chromium compound is complexed with certain ligands (e.g. picolinate or nicotinate) so as to be fully active. Since chromium supplementation increases insulin sensitivity in the insulin resistant state, this agent is expected to improve brain serotonin metabolism and thereby be of benefit in the management of obesity.

A further component of the composition of the invention is L-carnitine. L-carnitine serves as a carrier of long-chain fatty acids from the cytoplasm across the inner mitochondrial membrane to sites of beta-oxidation located in the inner mitochondrial matrix, thereby facilitating fat catabolism and yielding metabolic energy. L-carnitine has also been found to have a corrective effect on hypertriglyceridemia in type IV hyperlipoproteinemia. L-carnitine therapy also induces increased HDL cholesterol and decreased total cholesterol concentrations.

The mechanism whereby L-carnitine improves the respective metabolic disturbances remains to be investigated but, as is the case with chromium, an increase in insulin sensitivity seems to be a likely candidate in view of the reported metabolic effects of this agent. Moreover, markedly depressed plasma carnitine levels have been documented in the early stages of obesity suggesting a casual role.

In the view of the above, it is believed that obese subjects experience chromium and L-carnitine deficiencies, which may be a factor in the common treatment and failures of obesity through several mechanisms. It is believed that the chromium allows for fat to be converted into triglycerides and the L-carnitine allows the triglycerides to be catabolised.

For the purposes of the present description, St John's Wort Extract refers to an 8:1 concentration of the St John's Wort root product.

The invention will now be illustrated by the following non-limiting Examples in which a 0.3% extract of St John's Wort was used.

EXAMPLE 1

| Capsule containing: | |
| --- | --- |
| St John's Wort (hypericin) | 300 mg (0.9 mg) |
| chromium picolinate | 300 µg |
| L-carnitine | 25 mg |

EXAMPLE 2

| Capsule containing: | |
|---|---|
| St John's Wort (hypericin) | 150 mg (0.45 mg) |
| chromium polynicotinate | 300 μg |
| L-carnitine | 30 mg |

EXAMPLE 3

| Capsule containing: | |
|---|---|
| St John's Wort (hypericin) | 500 mg (1.5 mg) |
| chromium chelate | 500 μg |
| L-carnitine | 500 mg |

EXAMPLE 4

| Capsule containing: | |
|---|---|
| St John's Wort (hypericin) | 1 g (3 mg) |
| chromium proteinate | 500 μg |
| L-carnitine | 120 mg |

EXAMPLE 5

| Capsule containing: | |
|---|---|
| St John's Wort (hypericin) | 56.25 mg (0.16875 mg) |
| chromium picolinate | 200 μg |
| L-carnitine L-tartrate | 111 mg |

In terms of investigations carried out to date, daily dosages will usually contain approximately 20–75 mg St John's Wort Extract per day, conveniently as one capsule taken twice daily.

Further, non-limiting, examples utilising sibutramine hydrochloride monohydrate are set out below.

EXAMPLE 6

| Capsule containing: | |
|---|---|
| Sibutramine hydrochloride monohydrate | 5 mg |
| Chromium Picolinate/Polynicotinate | 200 μg |
| L-Carnitine | 100 mg |

Dosage: Take one capsule daily. May be increased to one capsule twice daily if necessary.

EXAMPLE 7

| Capsule containing: | |
|---|---|
| Sibutramine hydrochloride monohydrate | 10 mg |
| Chromium Picolinate/Polynicotinate | 300 μg |
| L-carnitine | 120 mg |

Dosage: Take one capsule daily. May be increased to one capsule twice daily if necessary.

EXAMPLE 8

| Capsule containing: | |
|---|---|
| Sibutramine hydrochloride monohydrate | 15 mg |
| Chromium Picolinate/Polynicotinate | 400 μg |
| L-carnitine | 150 mg |

Dosage: Take one capsule daily. May be increased to one capsule twice daily if necessary.

EXAMPLE 9

| Capsule containing: | |
|---|---|
| Sibutramine hydrochloride monohydrate | 20 mg |
| Chromium Picolinate/Polynicotinate | 500 μg |
| L-carnitine | 180 mg |

Dosage: Take one capsule daily. May be increased to one capsule twice daily if necessary.

It is envisaged that numerous variations may be made to the examples given above and the ratio of the various ingredients may be varied as may be required.

I claim:

1. A method of treating carbohydrate craving in a human patient comprising administering an anorexigenic composition comprising a compound which elevates serotonin levels in the brain of the patient in a mixture with a physiologically acceptable metabolisable chromium compound.

2. A method according to claim 1, wherein the compound which elevates serotonin levels in the brain is hypericin.

3. A method according to claim 2, wherein the hypericin is provided in the form of St John's Wort Extract.

4. A method according to claim 1, wherein the compound which elevates serotonin levels in the brain is sibutramine, or a salt thereof.

5. A method according to claim 4, wherein the sibutramine salt is sibutramine hydrochloride monohydrate.

6. A method according to claim 1, wherein the chromium compound is a bioavailable chromium compound.

7. A method according to claim 6, wherein the bioavailable chromium compound is chromium picolinate, chromium polynicotinate, chromium chelate or chromium proteinate.

8. A method according to claim 1, further comprising laevorotary carnitine or a racemic mixture of carnitine.

9. A method according to claim 8, wherein the anorexigenic composition is in a unit dosage form.

10. A method according to claim 9, wherein the dosage unit comprises:

10 mg–1000 mg St John's Wort Extract;

<1000 µg chromium compound; and 0 mg–500 mg L-carnitine.

11. A method according to claim 10, wherein the dosage unit is a capsule or tablet.

12. A method according to claim 11, wherein the capsule or tablet comprises from 20–150 mg St John's Wort Extract, 80–600 µg chromium compound; and 80–200 mg L-carnitine either alone or in a racemic mixture with D-carnitine.

13. A method according to claim 12, wherein the capsule or tablet comprises:

St John's Wort Extract: 20 mg–150 mg

Bioavailable chromium compound: 100 µg–300 µg

L-carnitine: 80 mg–150 mg.

14. A method according to any one of claims 10 to 13, wherein the dosage unit is administered as one capsule taken once to three times daily.

15. A method according to claim 9, wherein the dosage unit comprises:

1 mg–30 mg sibutramine;

100 µg–800 µg chromium compound; and 0 mg–800 mg L-carnitine.

16. A method according to claim 15, wherein the dosage unit is a capsule or tablet.

17. A method according to claim 16 wherein the sibutramine is in the form of sibutramine hydrochloride monohydrate and the capsule or tablet comprises from 5–20 mg sibutramine hydrochloride monohydrate, 100–600 µg chromium compound; and 100–180 mg L-carnitine either alone or in a racemic mixture with D-carnitine.

18. A method according to any one of claims 15 to 17 wherein the dosage unit is administered as a single capsule once or twice daily.

* * * * *